United States Patent [19]
Ho et al.

[11] Patent Number: 6,150,578
[45] Date of Patent: Nov. 21, 2000

[54] RECOVERY PROCESS FOR WET AROMATIC ALKYLATION AND DRY AROMATIC TRANSALKYLATION

[75] Inventors: Perry K. Ho, Wheeling; Russell C. Schulz, Glen Ellyn, both of Ill.

[73] Assignee: UOP LLC, Des Plaines, Ill.

[21] Appl. No.: 09/457,116

[22] Filed: Dec. 7, 1999

Related U.S. Application Data

[63] Continuation of application No. 08/967,138, Nov. 10, 1997, Pat. No. 5,998,684.
[60] Provisional application No. 60/034,282, Dec. 19, 1996.

[51] Int. Cl.[7] .............................. C07C 1/00; C07C 2/64; C07C 15/067; C07C 5/22; C07C 5/52
[52] U.S. Cl. .................... 585/323; 585/315; 585/316; 585/313; 585/449; 585/446; 585/470; 585/475
[58] Field of Search ..................... 585/323, 315, 585/316, 313, 449, 446, 470, 475

[56] References Cited

U.S. PATENT DOCUMENTS

| | | | |
|---|---|---|---|
| 4,008,290 | 2/1977 | Ward | 260/672 T |
| 4,051,191 | 9/1977 | Ward | 260/671 R |
| 4,083,886 | 4/1978 | Michalko | 260/672 T |
| 4,587,370 | 5/1986 | DeGraff | 585/450 |
| 4,695,665 | 9/1987 | DeGraff | 585/450 |
| 4,891,458 | 1/1990 | Innes et al. | 585/323 |
| 4,922,053 | 5/1990 | Waguespack et al. | 585/449 |
| 5,003,119 | 3/1991 | Sardina et al. | 585/323 |
| 5,030,786 | 7/1991 | Shamshoum et al. | 585/467 |
| 5,177,285 | 1/1993 | Van Opdorp et al. | 585/467 |
| 5,336,821 | 8/1994 | DeGraff et al. | 585/402 |
| 5,723,710 | 3/1998 | Gajda et al. | 585/467 |
| 5,902,917 | 5/1999 | Collins et al. | 585/323 |
| 5,998,684 | 12/1999 | Ho et al. | 585/323 |

FOREIGN PATENT DOCUMENTS 0 733 608 A1  9/1996  European Pat. Off. .

*Primary Examiner*—Jacqueline V. Howard
*Assistant Examiner*—Thuan D. Dang
*Attorney, Agent, or Firm*—John G. Tolomei; Michael A. Moore

[57] ABSTRACT

A separation arrangement for a cumene process that operates with a relatively wet feed to an alkylation zone and relatively dry feed to a transalkylation zone reduces utilities and capital expenses for the separation and recycle of distinct wet and dry components by using an arrangement that first separates effluent from the trans alkylation and alkylation reaction zone in a benzene column before performing light ends and drying in a downstream depropanizer column. The arrangement uses a portion of the net overhead stream from the benzene column as a wet recycle stream for return to the alkylation reaction zone and sends another portion of the benzene net overhead to the depropanizer to supply a dry benzene recycle for the trans alkylation reaction zone.

8 Claims, 1 Drawing Sheet

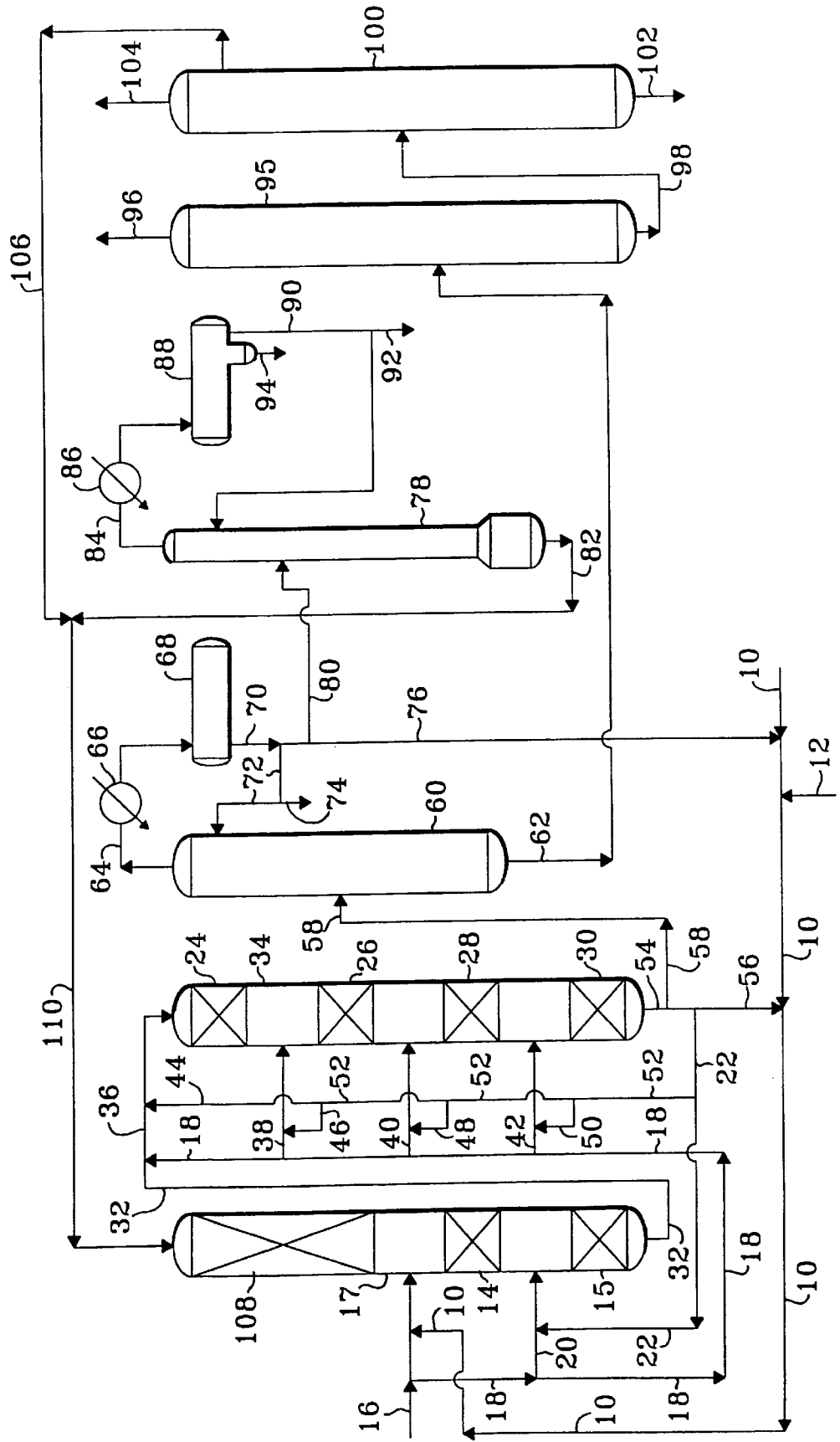

RECOVERY PROCESS FOR WET AROMATIC ALKYLATION AND DRY AROMATIC TRANSALKYLATION

CROSS-REFERENCE TO RELATED APPLICATION

This application is a continuation of U.S. application Ser. No. 08/967,138, filed on Nov. 10, 1997, now U.S. Pat. No. 5,998,684, which claims the benefit of U.S. Provisional Application No. 60/034,282, filed on Dec. 19, 1996.

FIELD OF THE INVENTION

The invention relates to a hydrocarbon conversion process. The invention more specifically relates to the production of alkylaromatic hydrocarbons by the reaction of an acyclic olefinic hydrocarbon with an aromatic feed hydrocarbon.

PRIOR ART

The alkylation of aromatic hydrocarbons such as benzene using solid catalysts is a well-developed art which is practiced commercially in large scale industrial units. One commercial application of this process is the alkylation of benzene with ethylene to produce ethyl benzene which is subsequently used to produce styrene. Another application is the alkylation of benzene with propylene to form cumene (isopropylbenzene), which is subsequently used in the production of phenol and acetone. Those skilled in the art are therefore familiar with the general design and operation of such alkylation process.

The prior art is well described in the literature. For instance, a typical flow scheme suitable for the commercial production of cumene is depicted in U.S. Pat. No. 4,051,191 issued to D. J. Ward. This reference describes in some detail, catalyst, reaction conditions, and separatory methods suitable for the recovery of cumene. The reactor effluent is passed into a rectification zone in which propane, charged to the process in admixture with the feed propylene, is separated for recycling and for rejection from the process. Liquid phase hydrocarbons recovered in the rectification zone are then passed into a two-column fractionation train comprising a recycle column and a cumene or product column. The benzene feed aromatic hydrocarbon is recycled from the top of the first fractionation column. The product cumene is recovered from the top of the second fractionation column, with heavy aromatic by-products being withdrawn from the bottom of the second column.

U.S. Pat. Nos. 4,695,665 and 4,587,370 issued to R. R. DeGraff are particularly directed to the separation of products and the recovery of recycle streams from processes for the alkylation of aromatic hydrocarbons and U.S. Pat. No. 4,695,665 discloses the use of a flash drum in combination with an effluent rectifier to recover unreacted feed components.

U.S. Pat. No. 4,083,886 describes a process for the transalkylation of the alkylaromatic hydrocarbons that uses a zeolitic catalyst.

U.S. Pat. No. 4,891,458 describes the use of beta zeolite for the alkylation of aromatic hydrocarbons with alkenes to produce polyalkylated aromatics.

U.S. Pat. No. 5,030,786 discloses an alkylation process wherein the feedstream is dehydrated to enhance the performance of beta or Y type zeolites in the alkylation process.

The performances of aromatic alkylation processes are influenced by the stability and activity of the catalysts in the operating environment of the process. Currently available catalysts for the alkylation of aromatic hydrocarbons typically require a high ratio of aromatic substrate to alkenes that improves the selectivity of the alkylation catalyst for the desired monoalkylated products. Nevertheless typical alkylation processes still produce a relatively large amount of polyalkylated aromatic products that are transalkylated by contact with a transalkylation catalyst and a additional aromatic substrate. Therefore, alkylation processes will typically have an alkylation zone and a transalkylation reaction zone.

U.S. Pat. No. 5,177,285 discloses an alkylation processes that is improved by maintaining the feed to the alkylation zone in a relatively wet condition and the feed to the transalkylation zone in a relatively dry condition. The process operates with a relatively pure ethylene feed as an alkylating agent with a large excess of benzene so that no light ends recovery is discussed.

BRIEF SUMMARY OF THE INVENTION

The principal object of this invention is to improve the performance of the separation section for a combined wet alkylation and dry transalkylation zone in a manner that facilitate the recovery of the necessary wet and dry streams while saving capital and utility costs.

This invention is the operation of a process for the production of alkylated aromatics using an alkylation zone and a transalkylation zone with a fractionation order that sends the effluent from the transalkylation zone first to a benzene recovery column before entering a C3 recovery zone that serves a combined function as a drier. The separation zone arrangement facilitates the recovery of unreacted aromatics and the polyalkyl aromatics as a transalkylation zone recycle stream and supplies the recycle stream with a low moisture content. Thus, the invention separates the alkylation zone product stream and the transalkylation zone product stream in a manner that conveniently reduces the water content of the unconverted aromatic hydrocarbon stream to a suitable level for use in the transalkylation zone. Lowering the moisture content of the transalkylation zone has the advantage of preserving the stability of the catalyst in the transalkylation zone.

The invention also facilitates the use of differing water contents in the transalkylation zone and particularly in the alkylation zone with a separation zone arrangement that provides capital and utility requirements over the usual separation arrangements. This invention is particularly useful where the alkylating stream is a relatively pure olefin stream having an olefin concentration of at least 90 wt %, preferably, the olefin concentration will be at least 99 wt % and more preferably at least 99.5 wt %.

Accordingly, in one embodiment this invention is a process for the production of alkylaromatic hydrocarbons. The process contacts a benzene-containing feed and an olefinic feed comprising ethylene or propylene in an alkylation reaction zone with an alkylation catalyst at alkylation conditions. The alkylation conditions can include a first water concentration that is advantageous to the overall operation of the alkylation process. The alkylation reaction zone produces an alkylation zone effluent comprising unconverted feed, aromatic hydrocarbons, mono-alkylated-aromatic hydrocarbons, and poly-alkylated-aromatic hydrocarbons. A relatively dry benzene recycle stream contacts a poly-alkylated-aromatic stream with a transalkylation catalyst in a transalkylation zone at transalkylation conditions that include a second water concentration which is less than the first water concentration to provide a transalkylation zone effluent. The transalkylation zone effluent and the alkylation zone effluent enter a benzene separation zone that separates benzene and lower boiling materials from the monoalkylated and polyalkylated aromatic hydrocarbons to produce a first bottom stream that comprises the monoalkylated and polyalkylated hydrocarbons and a benzene cut that contains water, benzene, and $C_3$ or lighter hydrocarbons. At least a portion of the benzene cut passes through a light ends column that separates benzene from water and $C_3$ or lighter hydrocarbons to produce the relatively dry benzene stream that has a lower water concentration than the first water concentration and a light stream that is withdrawn from the process. The process separates the first bottom stream into a product stream of monoalkylated aromatics and second bottom stream of polyalkylated aromatics. The second bottom stream is separated into a heavy stream that is removed from the process and the polyalklyated aromatics stream.

In a more specific embodiment, this invention is a process for the production of cumene. The process contacts benzene and an alkylate feed comprising propylene and propane in an alkylation reaction zone with an alkylation catalyst at alkylation conditions including a water concentration of typically about 50 wppm to produce an alkylation effluent comprising water, propane, benzene, cumene, and heavier hydrocarbons. The water concentration in the alkylation zone will usually be a function of the water concentration of the entering propylene feed which in most cases will have a saturated water concentration of 50 wppm. A relatively dry benzene recycle stream contacts a diisoproplybenzene stream with a transalkylation catalyst in a transalkylation reaction zone at transalkylation conditions to provide a transalkylation zone effluent. The conditions in the transalkylation zone include a water concentration less than the water concentration in the alkylation zone or in any case less than 200 wppm. A benzene separation zone separates the alkylation zone effluent into a benzene cut comprising benzene, propane, and water and a benzene bottoms that includes cumene, diisopropyl benzene, and heavier hydrocarbons. A light ends column separates the benzene cut into lighter components comprising water and propane and heavier components comprising a relatively dry benzene stream having a water concentration of less than 200 wppm, preferably less than 50 wppm and more preferably less than 20 wppm. The benzene bottoms undergoes further separation into a product stream comprising cumene and a cumene bottoms stream that include diisopropyl benzene and higher boiling hydrocarbons. The cumene bottom stream is separated into a heavy stream that is removed from the process and a diisopropyl benzene stream that returns to the transalkylation zone.

Other objects, embodiments, and details of this invention can be found in the detailed description of the invention.

BRIEF DESCRIPTION OF THE DRAWING

The description of this invention in the context of the specific process for the production of cumene is not meant to limit this invention to the specific details or the process disclosed in the above described FIGURE.

The FIGURE schematically illustrates the major equipment used in performing the process of this invention for the production of cumene. In the process, benzene carried by a line 10 is admixed with water from a line 12 and enters a bed of zeolitic alkylation catalyst 14 along with a propylene feed from a line 16. A vessel 17 houses alkylation catalyst bed 14 and an additional alkylation catalyst bed 15. After contact with the catalyst in bed 14, effluent from bed 14 flows through the reactor and receives additional propylene via lines 18 and 20 along with an optional recycle of alkylation zone effluent via line 22. Alkylation zone effluent from bed 15 flows from vessel 17 into a vessel 34 and through another series of alkylation beds 24, 26, 28, and 30 that all contain a zeolitic alkylation catalyst. Line 18 supplies additional propylene upstream of each additional alkylation bed through lines 36, 38, 40, and 42. Again, an optional recycle of alkylation zone effluent may also enter upstream of each additional alkylation bed 24, 26, 28 and 30 through lines 44, 46, 48, and 50 respectively which each receive the alkylation zone effluent from a line 52. The alkylation zone effluent flows from alkylation bed 30 out of vessel 34 via a line 54. Line 54 supplies the optional alkylation zone effluent to the alkylation zones via line 22 and to the first alkylation zone via a line 56. The remaining alkylation zone effluent flows through a line 58 into a benzene column 60 that withdraws a benzene cut containing benzene and lower boiling hydrocarbons via a line 64 and a bottom stream 62 of higher boiling hydrocarbons. The benzene cut passes through a cooler 66 and enters a receiver 68. The benzene cut also contains propane or lighter boiling materials that exit receiver 68 with benzene via line 70. Reflux flows back to column 60 via a line 72. A line 74 withdraws a benzene drag stream. Line 76 returns a portion of the benzene cut containing a relatively high water concentration returns to the alkylation zone. Line 80 passes the remainder of the benzene cut to a depropanizer 78. Depropanizer 78 recovers a purified benzene stream 82 having a relatively low water concentration. Line 84 passes an overhead stream from column 78 through a cooler 86 and into a receiver 88. Receiver 88 separates water via boot line 94 to produce a reflux stream 90 from which line 92 recovers propane. Line 62 carries benzene column bottoms to a cumene column 95. Line 96 recovers a cumene product overhead and line 98 transfers a bottoms stream to a heavies column 100 for the recovery of diisopropyl benzene via a line 106, lighter boiling material via a line 104 and heavy aromatics via a line 102. A purified stream of diisopropyl benzene returns as recycle via line 106 in combination with benzene from line 82 carried by a line 110 into a bed of zeolitic transalkylation catalyst 108 contained in vessel 17. Effluent from the transalkylation zone flows through vessel 17 to the top of alkylation catalyst bed 14.

DETAILED DESCRIPTION OF THE INVENTION

This invention is suitable for aromatic and olefinic feedstocks. Suitable aromatic feed hydrocarbons for this invention include various aromatic substrates. Such substrates can be alkylated aromatic hydrocarbons such as alkyl substituted benzenes but are preferably unsubstituted benzenes. The alkylating agent that may be used in the alkylation reaction zone includes monoolefins, diolefins, polyolefins, acetylenic hydrocarbons and other substituted hydrocarbons but are preferably $C_2$–$C_4$ hydrocarbons. In the most preferred form of this invention, the alkylation agent will comprise ethylene and propylene.

A catalyst promotes the initial alkylation in the alkylation reaction zone. A wide variety of catalysts can be used in the alkylation reaction zone. Suitable catalysts for use in the reaction zone will comprise any catalyst that does not suffer deleterious effects from the presence of water. Preferably a substantial quantity of water may be tolerated or desired in the presence of the alkylation catalyst. A substantial quantity of water preferably means a water concentration in the reactants entering the alkylation zone of at least 50 wppm. The alkylation reaction zone may have a water content of over 200 wppm and up to 500 ppm or more. The preferred catalyst for use in this invention is a zeolitic catalyst. The catalyst of this invention will usually be used in combination with a refractory inorganic oxide binder. Preferred binders are alumina or silica. Preferred alkylation catalysts are a type Y zeolite having an alumina or silica binder or a beta zeolite having an alumina or silica binder. The zeolite will be present in an amount of at least 50 wt. % of the catalyst and more preferably in an amount of at least 70 wt. % of the catalyst.

The alkylation reaction zone can operate under a broad range of operating conditions. Temperatures usually range from 100° C. to 325° C. with the range of about 150–275° C. being preferred. Pressures can also vary within a wide range of about 1 atmosphere to 130 atmospheres. Since liquid phase conditions are generally preferred within the reaction zone, the pressure should be sufficient to maintain the reactants in such phase and will typically fall in a range of from 10 to 50 atmospheres. Reactants generally pass through the alkylation zone at a mass flow rate sufficient to yield a liquid hourly space velocity from 0.5 to 50 $hrs^{-1}$ and especially from about 1 to 10 $hrs^{-1}$.

The alkylation zone is ordinarily operated to obtain an essentially complete conversion of the alkylating agent to monoalkylate and polyalkylate. To achieve this effect, additional aromatic substrate will usually be charged to the reaction zone. Thus, the feed mixtures are introduced into the reaction zone at a constant rate and a molecular ratio of about 1:1 to 20:1 aromatic substrate to alkylating agent with a ratio of about 2:1 to 10:1 being preferred. As a result, in addition to product there will usually be a substantial amount of unreacted aromatic substrate that is removed with the product stream from the alkylation reaction zone.

This invention is particularly applicable to case where the monoalkylate agent contains non-alkylating materials and preferably in low concentrations. For example, in the production of cumene with benzene and a propylene alkylating agent, the propylene-containing stream will also contain propane. This invention is typically suitable where the propylene stream contains from 0 to 10 wt % propane, and more preferably, the propylene stream contains from 0 to 0.5 wt % propane.

As mentioned the alkylation reaction zone will often provide a wide variety of undesired by-products. For example, in the alkylation of benzene with ethylene to produce ethylbenzene, the reaction zone can also produce di- and triethylbenzene in addition to other ethylene condensation products. Similarly, in the alkylation of benzene with propylene to produce cumene, the reaction zone can produce di and tri isopropylbenzene in addition to still more condensation products. The transalkylation arrangement of this invention dealkylates the polyalkylated products in the presence of additional substrate to yield additional alkylate products. Therefore, a number of separation stages are needed to separate aromatic products from the additional by-products.

A number of combinations of columns and separators can be used to recover the desired alkyl aromatic product and produce recycle streams of aromatic substrate and polyalkylated aromatics for transalkylation. This invention used a separation arrangement that has a first column to separate the aromatic substrate from the remaining heavier components of the product effluent. One or more additional separation columns will fractionate the aromatic product from lighter or heavy by-product streams. Heavy components that are not suitable for transalkylation are usually rejected from the process.

In the case of cumene production the alkylation reaction zone effluent will enter a benzene column from which a benzene cut is withdrawn as a sidecut or overhead while higher boiling reaction products are passed on to a cumene column from which cumene product is withdrawn as an overhead. The higher boiling products from the cumene column enter the heavies column which fractionates the polyalkylated benzene into an overhead stream for use as feed to the transalkylation reactor and provides a bottoms stream of heavier hydrocarbons that are rejected from the process.

Common past arrangements for the recovery of aromatic substrate recovered benzene as the overhead from a fractionation column. An overhead condenser has been used for the separation of water from the overhead stream and a portion of the aromatic hydrocarbon condensate returns to the column as reflux while the remainder is split between the alkylation reactor and transalkylation reactor. Removal of water from the overhead is difficult due to the high solubility of water in benzene. Traditionally, the overhead condenser was operated to reduce the water concentration to a level of about 550 wt. ppm. Although such water concentrations were acceptable and in many cases beneficial to the alkylation reactor operation, the same water concentrations have been found to have a deleterious effect on the zeolitic catalyst in the transalkylation reactor. Therefore, many separation arrangements required further drying of that portion of the aromatic substrate that is returned from the overhead condenser to a transalkylation reactor.

This invention sends a benzene cut to a light ends column that removes light hydrocarbon components and water to supply an aromatic substrate having a low water concentration while eliminating light materials. The aromatic substrate is typically withdrawn as a bottom stream from the column. The light ends column typically reduces the bottoms stream water concentration to less than 200 wt. ppm. The use of the light ends column provides a highly efficient method for also removing water from the recirculating aromatic substrate i.e., benzene. It has been proposed to remove water in the upper portion of the benzene column or in the benzene column receiver. However, this requires sub-cooling of the benzene column receiver which is neither efficient nor effective. It conserves utilities to operate the benzene column receiver at its bubble point and to transfer the net benzene for return to the transalkylation zone through the light ends column.

Therefore, in accordance with this invention, the light ends separation column operates to withdraw net overhead streams of water and light ends and a relatively dry bottoms stream returns aromatic substrate to the transalkylation reactor. Relatively dry means that the recycle steam has a water concentration of less than 200 wppm. Again, in the context of cumene separation, the modification of placing a depropanizer column downstream of a benzene column accomplishes the required degree of benzene drying while also removing light ends. A portion of the benzene column overhead effluent is split on control to supply the benzene requirements of the transalkylation zone and sent to the light ends column. A small drag stream of the overhead from the benzene column can be removed to take non-aromatic $C_6$ hydrocarbons out of the system. The volume of low moisture content aromatic substrate needed from the light ends column will usually will be balanced by diverting the excess benzene cut into the alkylation reactor.

As stated the alkylation reaction zone produces polyalkylated aromatic compounds as well as the desired monoalkylated aromatic product. These polyalkylated aromatics contact additional aromatic substrate in a transalkylation reactor to produce additional monoalkylated product. The transalkylation reaction zone of this invention will use a zeolitic catalyst. The zeolite will be present in an amount of at least 50 wt. % of the catalyst and more preferably in an amount of at least 90 wt. % of the catalyst. In most cases the zeolitic catalyst again includes an inorganic oxide binder. The preferred inorganic oxide for use in the transalkylation catalyst is alumina with gamma-alumina, eta-aluminum and mixtures thereof being particularly preferred. The zeolite may be present in a range of from 5 to 99 wt. % of the catalyst and the refractory inorganic oxide may be present in a range of from 5 to 95 wt. %. Preferred transalkylation catalysts are a type Y zeolite having an alumina or silica binder or a beta zeolite having an alumina or silica binder.

Again water has been found to have a deleterious effect on many catalyst and in particular zeolitic catalysts. In order to sustain adequate conversion from the transalkylation zone over a normal run period, the loss in activity is compensated by increasing severity of operation within the reaction zone. The increase in severity causes the transalkylation reactor to lose selectivity and ultimately results in a shortened length of run for the catalyst, a loss in product yields, or combination of the two. By operating the transalkylation reaction zone at a lower water concentration than the alkylation reaction zone, typically a water concentration of less than 200 wppm, loss of activity in the transalkylation zone is kept at reasonable levels. Preferably the water concentration in the transalkylation zone will be less than 20 wppm and more preferably below 5 wppm.

There is no requirement that the alkylation reaction zone and the transalkylation reaction zone use the same catalyst. This process is useful for any arrangement of alkylation reaction zone and transalkylation reaction zone wherein the operation of the former is benefited by a high water concentration and a high water concentration in the latter is detrimental. However, it has been found that a beta zeolite or a high Y type zeolite contained in an alumina binder will perform very well when used in both the alkylation reaction zone and the transalkylation reaction zone. Therefore, in the preferred embodiment of this invention, both reaction zones will use the same catalyst.

The transalkylation reaction can be carried out in a broad range of operating conditions that include a temperature of from 100–390° C. and pressure ranging from 1 to about 130 atmospheres. Again, the pressure would generally be selected so that the reactants will remain in the liquid phase. Accordingly, preferred pressures for the transalkylation reaction zone range from 10 to about 50 atmospheres. A liquid hourly space velocity of from 0.5 to 50 $hrs^{-1}$ is desirable for the transalkylation reaction zone with LHSV of from 0.5 to 5 $hrs^{-1}$ being preferred.

The transalkylation and alkylation reaction zones may be operated and arranged in any manner that provides the desired operating temperatures and number of contacting stages. Multiple contacting stages in the alkylation zone are routinely used to provide cooling by staged addition of reactants to multiple beds of alkylation catalyst. The multiple injection of the reactants serves to cool the stages between alkylation catalyst beds and provide temperature control. The alkylation catalyst is ordinarily arranged in multiple beds to permit interbed injection of alkylating agent. The separate alkylation catalyst beds may be arranged in a single vessel or in multiple vessels. This invention can be used with a traditional parallel arrangement for the alkylation zone and the transalkylation zone where feed streams are sent independently to each reaction zone. Preferably the reaction zone will have a series flow arrangement with the dialkylated benzene passing first to the transalkylation zone with a large excess of benzene that passes next through a series of alkylation catalyst beds with interstage injection of alkylating agent and any additional quantities of benzene. In the series flow arrangement a common vessel may contain a transalkylation reaction zone and one or more alkyaltion reaction zones as depicted in the FIGURE. For very large units, separate vessels for the transalkylation catalyst bed and one or more of the alkylation catalyst beds may be more advantageous.

The beneficial operation of this invention will be further described in the context of an exemplified preferred embodiment which is the alkylation of propylene with benzene to obtain cumene. Both of these examples presented herein are based on engineering calculations and actual operating experience with similar processes. In describing these examples, valves, pumps, feeders, instruments and heat exchangers other than those necessary for an understanding and appreciation of the invention have been omitted.

EXAMPLE I

The flow scheme for this example is substantially that shown in the FIGURE, except for the rearrangement of the benzene and lights ends column. This example shows the performance of a cumene process arranged in accordance with the prior art wherein a serial flow effluent from an alkylation zone is passed first through a light ends column for removal of a net propane overhead and then to a benzene column The reactor arrangement is the same as that shown in the FIGURE. As opposed to the FIGURE, a depropanizer column first receives the effluent from the alkylation reaction zone and passes a bottom stream to a benzene column.

Accordingly, the process operates by combining fresh benzene feed with a recycle stream of benzene recovered from a benzene column. The fresh benzene feed has a purity of approximately 99.91 mol %. Water is added to the benzene feed as water makeup for obtaining a water concentration of about 100 wppm in the alkylation reaction zone. A first quantity of propylene feed having a purity of 99.6 mol %, is mixed with the combined benzene feed and enters an inlet of an alkylation reaction zone where it is combined with the effluent from a herein described transalkylation zone. The benzene and propylene feed components pass through a series of 6 separate alkylation beds having at a space velocity of about 0.5. Following the first alkyaltion bed each subsequent bed receives staged injection of an equivalent quantity of propylene feed. The propylene feed contains trace amounts of propane and has a temperature of approximate 100° F. to provide cooling to the alkylation reaction beds. The alkylation reaction zone operates at a temperature of from 260° F. to approximately 300° F. at the last alkylation reaction bed and at a pressure of about 400 psig. The alkylation reaction zone operates with a phenyl to propyl molar ratio of about 3.

An effluent stream of about having the composition given for stream A in Table 1, passes to a depropanizer column. Net component streams of about 2½ lb-mol/hr of propane and 1.4 lb-mol/hr of water are withdrawn from the overhead of the depropanizer column. The bottom stream from the depropanizer enters a benzene column which operates at a temperature and pressure of approximately 56 psig and 280° F. The benzene column produces a net overhead stream containing approximately 90 mol % benzene with the majority of the balance consisting of $C_6$ paraffins. A small drag stream of $C_6$ hydrocarbons is withdrawn from the net overhead of the benzene column. A net bottom stream having the composition given for stream B in Table 1 leaves the benzene column at a temperature of about 470° F. and a pressure of about 67 psig and enters a cumene column from which cumene having a purity of approximately 99.97% is withdrawn as an overhead stream. The remaining net bottom stream from the cumene column enters a heavy ends column that removes a net bottoms stream. The net bottoms stream from heavy ends column contains about 55 mol % $C_{13}$ and higher hydrocarbons about 25 mol % diisopropyl benzene and with the remainder consisting of lighter materials. The heavy ends column also discharges a net overhead drag stream of approximately 1 lb mol/hr containing approximately 70% cumene. The heavy ends column produces a net sidecut stream having composition given for stream C in Table 1. The sidecut returns to the transalkylation zone with approximately 67% of the net overhead from the benzene column returns as the feed to the transalkylation reactor at a combined temperature of about 275° F. and 450 psig. Water concentration in the feed to the transalkylation zone is less than 20 wppm. The remaining portion of the overhead stream from the benzene column is combined as recycle to the alkylation reaction zone.

The transalkylation reaction zone operates at a temperature of about 275° F. and a pressure of about 45 psig. The transalkylation feed moves through a zeolite catalyst in the transalkylation reaction zone at an LHSV of approximately 0.6. The transalkylation zone operates with a phenyl to propyl molar ratio of approximately 4.

Accordingly, the separation section of the alkylation and transalkylation reaction zones includes depropanizer column, benzene column, a cumene column, and a heavies column for removal and recovery of diisopropyl benzene. The size, operating conditions and duties for each column are listed in Table 2.

EXAMPLE II

The flow scheme for this example is that shown in the FIGURE. The flow scheme of this example is essentially the same as that described in Example 1 except for the innovation of this invention that delivers the net effluent from the alkylation reactors directly to a benzene column and then transfers a portion of the net overhead from the benzene column to a depropanizer column. As shown in the FIGURE, the overhead from the depropanizer column then supplies the benzene recycle to the transalkylation reaction zone. Unless otherwise specified, all of the operating conditions and physical characteristics of the alkylation, transalkylation, and separation sections are otherwise the same for Examples I and II.

The transalkylation and alkylation reaction zones receive essentially the same feed as that previously described in Example 1 and operates at essentially the same conditions and in the same manner. The effluent from the alkylation reaction zones has the composition given for stream D in Table 1. Approximately 33% of the net overhead from the benzene column is recycled directly as the feed to the alkylation reaction zone and has a water content of about 260 wppm. A small net portion of the benzene overhead is again withdrawn as purge. The stream to the benzene column has the composition given for stream D in Table 1.

The benzene column bottoms obtained in this Example is essentially the same as that obtained in Example I and has the composition given for stream E in Table 1 The benzene column bottom again pass through a cumene column to recover an overhead having a 99.97 mol % purity cumene product with the remaining bottoms portion of the stream passing to a heavies column. The heavies column removes a small net bottom stream which contains approximately 55% $C_{13}$ and heavier hydrocarbons and 28% diisopropyl benzene with the remainder comprising lighter materials. The heavy column again provides a net overhead drag of approximately of less than 10 lb mol/hr comprising 70% cumene. The sidecut from the heavies column has the composition given for stream F in Table 1.

The net overhead from the benzene column has the composition given in Table 1 for stream G. Less than 10 lb/hr of the net benzene column overhead leaves the process as a drag stream with the remainder returning directly to the alkylation zone in combination with the benzene feed stream. The remainder of the net benzene overhead passes to the depropanizer. The depropanizer withdraws net overhead component streams comprising less than 10 lb-mol/hr of propane and less than 2 lb-mol/hr of water. The remainder of the input to the depropanizer passes out of the column as a bottom stream that returns in combination with the diisopropyl benzene to the transalkylation zone at a temperature of 275° F. and a pressure of 450 psig and a water concentration of less than 20 wppm.

Again, the separation section for Example II includes depropanizer column, benzene column, a cumene column, and a heavies column for removal and recovery of diisopropyl benzene. The size, operating conditions and duties for each column are listed in Table 3.

A comparison of the process streams two examples shows that both examples provide essentially the same amount of product. The main differences are in the size of the separation equipment required and the utilities used therein. In Example II, the separation columns use the same number of theoretical trays as the columns described for Example 1. However, the depropanizer column size has been reduced to an upper diameter of about 2½ ft and a lower diameter of about 5½ ft. The benzene column can also now be operated as split column with a diameter of about 6½ ft in an upper section and a lower diameter of 8 ft. Thus there is no significant change in capital costs for the benzene columns between the two examples. The cumene column and heavies column are approximately the same size. Accordingly, from a capital standpoint, the invention as applied to the cumene process reduces the size requirements of the column substantially.

A further comparison of the Tables demonstrates an approximate 10% savings in condenser duty with no increase in reboiler duty. Accordingly, a comparison of Tables 2 and 3 demonstrate capital and utility advantages for the arrangement of this invention over the prior art.

TABLE 1

Relative Stream Compositions - Mol %

| Stream Compon. | A | B | C | D | E | F | G |
|---|---|---|---|---|---|---|---|
| Water | .05 | | | .08 | | | .11 |
| C3 olefin | | | | | | | |
| C3 paraffin | .10 | | | .14 | | | .21 |
| C6 paraffin | 1.39 | | | 1.13 | | | 1.63 |
| C6 cyclic | 4.85 | | | 3.68 | | | 5.30 |
| Benzene | 62.96 | | | 63.93 | | | 92.2 |

TABLE 1-continued

Relative Stream Compositions - Mol %

| Stream Compon. | A | B | C | D | E | F | G |
|---|---|---|---|---|---|---|---|
| C7 | .08 | | | .01 | | | .01 |
| Toluene | .01 | .01 | | .01 | | | .02 |
| Cumene | 24.27 | 79.10 | .08 | 24.64 | 79.2 | .08 | .5 |
| NC3 Benz. | | .02 | | | .02 | | |
| Cymene | | .01 | .04 | .1 | .03 | .08 | |
| C11 Phenyl | | | .03 | | | .03 | |
| C11 Arom. | | | .02 | | | .02 | |
| C12 Phenyl | .2 | .68 | 3.28 | .21 | .68 | 3.36 | |
| C12 Arom. | .01 | .05 | .05 | .01 | .05 | .06 | |
| TMIND | .02 | .07 | .34 | .02 | .07 | .36 | |
| DIPB | 5.97 | 19.78 | 96.15 | 6.07 | 19.78 | 96.57 | |
| $C_{13}+$ | .05 | .15 | .01 | .05 | .15 | .02 | |

TABLE 2

| Column | Depropanizer | Benzene | Cumene | Heavies |
|---|---|---|---|---|
| I.D. Top ft. | 4 | 7 | 10 | 5 |
| I.D. Bottom ft. | 8 | 7 | 10 | 5 |
| Receiver Temp. F | 115 | 283 | 332 | 328 |
| Receiver PSIG | 217.6 | 56 | 6.0 | 15.7 |
| Reboiler Duty MMBTU/HR | 26.9 | 25.1 | 26.9 | 7.9 |
| Condensor Duty MMBTU/HR | 8.5 | 37 | 33.4 | 8.6 |

TABLE 3

| Column | Depropanizer | Benzene | Cumene | Heavies |
|---|---|---|---|---|
| I.D. Top ft. | 2.5 | 6.5 | 10 | 5 |
| I.D. Bottom ft. | 5.5 | 8.0 | 10 | 5 |
| Receiver Temp. F | 114 | 278 | 332 | 329 |
| Receiver PSIG | 217.6 | 56 | 6.0 | 15.7 |
| Reboiler Duty MMBTU/HR | 9.5 | 38.4 | 30.0 | 7.9 |
| Condensor Duty MMBTU/HR | 2.8 | 32.1 | 36.5 | 8.6 |

What is claimed is:

1. A process for the production of alkylaromatic hydrocarbons which comprises:

a) contacting benzene containing feed and an olefinic feed comprising ethylene or propylene in an alkylation zone with an alkylation catalyst at alkylation conditions and recovering an alkylation zone effluent comprising unconverted feed aromatic hydrocarbons, monoalkylated aromatic hydrocarbons, and polyalkylated aromatic hydrocarbons;

b) contacting a benzene recycle stream and a polyalkylated aromatic stream with a transalkylation catalyst in a transalkylation zone at transalkylation conditions to provide a transalkylation zone effluent, wherein the transalkylation zone and alkylation zone are arranged for series flow and the transalkylation zone effluent is passed with the benzene containing feed and the olefinic feed to the alkylation zone;

c) passing the alkylation zone effluent to a benzene separation zone and separating benzene and lower boiling materials from the monoalkylated and polyalkylated aromatic hydrocarbons to produce a bottoms stream comprising monoalkylated and polyalkylated hydrocarbons, the benzene recycle stream having a water concentration of less than 200 wppm, and a light stream that is withdrawn from the process;

d) separating the bottoms stream into a product stream of monoalkylated aromatics and the polyalkylated aromatic stream.

2. The process of claim 1 wherein said olefinic feed comprises propylene.

3. The process of claim 1 wherein the transalkylation conditions include a water concentration not in excess of 200 wppm.

4. The process of claim 1 wherein said alkylation and transalkylation catalysts comprise a zeolite and alumina.

5. The process of claim 4 wherein said alkylation and transalkylation catalysts comprise alumina and at least 50 wt. % Y-zeolite.

6. The process of claim 1 wherein said alkylation and transalkylation catalysts have the same composition.

7. The process of claim 1 wherein said water concentration in said transalkylation reaction zone is less than 20 wppm.

8. The process of claim 1 wherein said olefinic feed comprises at least 90 wt % olefins.

* * * * *